United States Patent [19]

Hager

[11] 4,313,006

[45] Jan. 26, 1982

[54] PROCESS FOR CONVERTING DIALKYL SULFIDES TO ALKYL MERCAPTANS

[75] Inventor: Robert B. Hager, Collegeville, Pa.

[73] Assignee: Pennwalt Corporation, Philadelphia, Pa.

[21] Appl. No.: 183,705

[22] Filed: Sep. 3, 1980

[51] Int. Cl.$^3$ ............................................. C07C 148/00
[52] U.S. Cl. ......................................... 568/70; 568/61
[58] Field of Search ....................... 568/70, 60, 58, 61, 568/68

[56] References Cited

U.S. PATENT DOCUMENTS

| | | | |
|---|---|---|---|
| 2,816,146 | 12/1957 | Doumani | 568/60 |
| 2,910,506 | 10/1959 | Folkins et al. | 568/60 |
| 4,005,149 | 1/1977 | Kubicek | 568/70 |
| 4,059,636 | 11/1977 | Kubicek | 568/70 |
| 4,102,931 | 7/1978 | Buchholz | 568/73 |

FOREIGN PATENT DOCUMENTS

| | | | |
|---|---|---|---|
| 45-05531 | 2/1970 | Japan | 568/68 |
| 52-46203 | 11/1977 | Japan . | |
| 274095 | 9/1970 | U.S.S.R. | 568/70 |

*Primary Examiner*—Donald G. Daus
*Assistant Examiner*—Diana G. Rivers

[57] ABSTRACT

A process is provided for preparing alkyl mercaptans by reacting a dialkyl sulfide with hydrogen sulfide in the presence of a zeolite catalyst.

13 Claims, No Drawings

PROCESS FOR CONVERTING DIALKYL SULFIDES TO ALKYL MERCAPTANS

BACKGROUND OF THE INVENTION

This invention relates to a continuous vapor-phase process for the manufacture of alkyl mercaptans by reacting a dialkyl sulfide with hydrogen sulfide in the presence of a zeolite catalyst.

Alkyl mercaptans are produced commercially either by reacting an alkyl alcohol with hydrogen sulfide or by the addition of hydrogen sulfide to an alkene. In either case, the major by-product is the corresponding dialkyl sulfide, formed by the equilibrium reaction,

2 RSH⇌RSR+H₂S.

There are commercial applications for certain dialkyl sulfides, but in most cases the dialkyl sulfides obtained as by-products in mercaptan-manufacturing processes are contaminated with a number of other by-product impurities that make them difficult and uneconomical to purify, and they must, therefore, be disposed of as chemical waste.

One possible method to reduce the volume of the by-product sulfide waste and to recover economic value from it, is to react it with hydrogen sulfide, thereby reconverting the major dialkyl sulfide component of the waste to alkyl mercaptan according to the reverse of the above equilibrium reaction. Several procedures for cracking symmetrical dialkyl sulfides with hydrogen sulfide to form the corresponding alkyl mercaptan are described in the prior art. Beach, et al. (U.S. Pat. No. 2,667,515) provided a process for converting dimethyl sulfide and hydrogen sulfide to methyl mercaptan over a catalyst consisting of 10% cadmium sulfide on alumina at about 400° C. Single-pass molar conversions to methyl mercaptan of about 59% were obtained. A Japanese patent (No. 77046203) discloses the use of a tungsten trisulfide on alumina catalyst at 320°-450° C.

Kubicek (U.S. Pat. No. 4,005,149) discloses the use of carbon disulfide, as a reaction promoter, in the presence of sulfactive catalysts such as cobalt molybdate on alumina to enhance conversions to alkyl mercaptan at lower reaction temperatures. Molar ratios of dialkyl sulfide/carbon disulfide ranging from about 0.1/1 to about 50/1 are employed and the process is shown in the examples to be operable for dialkyl sulfides ranging from dimethyl sulfide to di-n-dodecyl sulfide (dialkyl sulfides up to C₄₀ are claimed). Catalyst temperatures in the range of about 400° F. (204° C.) to about 600° F. (316° C.) can be used. In U.S. Pat. No. 4,059,636, Kubicek further discloses the use of a supported phosphotungstic acid catalyst, a preferred embodiment being that carbon disulfide is also present in the reaction mixture to enhance the conversion of dialkyl sulfide to alkyl mercaptan at lower temperatures. Example 2 shows appreciably lower conversions, especially at the lower temperatures (204°-288° C.), when carbon disulfide is not used in conjunction with the phosphotungstic acid catalyst. Example 3 teaches that when dibutyl sulfide containing 24 mole % carbon disulfide is reacted with hydrogen sulfide over a phosphotungstic acid on alumina catalyst at 500°-550° F. (260°-288° C.), a single-pass molar conversion of di-n-butyl sulfide to n-butyl mercaptan of about 65% is obtained [i.e., percent conversion to C₄H₉SH is percent total conversion of (C₄H₉)₂S X % selectivity to C₄H₉SH/100].

STATEMENT OF THE INVENTION

This invention is directed to a continuous, vapor-phase process for preparing C₁ to C₁₈ alkyl mercaptan (RSH) that comprises reacting a dialkyl sulfide, R—S—R, where R is C₁ to C₁₈ alkyl or C₆ to C₁₈ cycloalkyl, with a molar excess of hydrogen sulfide in the presence of a zeolite catalyst at elevated temperatures, said zeolite catalyst being Type X, Type Y or Type L, and containing less than 10% by weight of an alkali weight, expressed as Na₂O.

DEFINITIONS

A class of catalysts has been found that permits improved conversions of dialkyl sulfides and hydrogen sulfide to alkyl mercaptans at relatively low temperatures without the need for a reaction promoter such as carbon disulfide in the process. The economic advantages of being able to operate at lower temperatures without having to feed, separate, and recycle appreciable quantities of a reaction promoter are obvious to anyone familiar with the operation of continuous, catalytic processes. The catalyst of this invention belongs to the family of zeolites, which are synthetic aluminosilicates of well-defined chemical composition and physical structure.

Excellent results are obtained in the reaction of dialkyl sulfides with hydrogen sulfide (H₂S) to form alkyl mercaptans (RSH), where R is a primary, secondary, or tertiary alkyl, or a cycloalkyl group, containing from 1 to 18 carbons (C₁ to C₁₂ alkyl being preferred) when said reaction is carried out in the presence of a synthetic zeolite catalyst having an alkali metal content (expressed as Na₂O) of less than 10% by weight.

The zeolite (or molecular sieve) catalysts are synthetic aluminosilicates characterized by high uniformity, well-defined pore size, large surface area, complete crystallinity and excellent reproducibility. Their structures are described in the Union Carbide booklet F-08 entitled, "Linde Molecular Sieve Catalysts," and D. W. Breck's textbook, "Zeolite Molecular Sieves", John Wiley & Sons (1974).

The basic structural units of synthetic zeolites are Si and Al atoms tetrahedrally coordinated with four oxygen atoms. The oxygen atoms are mutually shared between tetrahedral units contributing one of the two valence charges of each oxygen atom to each tetrahedron. Since aluminum atoms are trivalent, each AlO₄⁻ is negatively charged. The charge on these units is balanced by cations, generally Na+ or K+, in the as-synthesized zeolites. These cations are exchangeable with other cations. For example, a divalent caton such as cobalt or nickelous nickel will replace 2 univalent cations; a trivalent cation such as chromium, lanthanum, or cerium will replace 3 univalent cations; and a tetravalent cation such as thorium will replace 4 univalent cations. It is thus possible to replace the alkali metal cations Na+ or K+ with catalytically more active cations such as Ni+2, Co+2, Fe+2, or +3, Mo+2, or +3, Cr+3, La+3, Th+4, etc., if desired.

Although many factors influence the catalytic activity of these zeolites, the three most important are: (1) the open framework structure with its attendant pore size, (2) the SiO₂:Al₂O₃ ratio of the framework, and (3) the cations.

As in most commercial catalytic conversion processes, however, only the large-pore zeolites having pore openings in the range of 7 to 10 Angstroms (A) are useful. The two most preferred are Type X and Type Y zeolites. The Type L, more siliceous than Type X and Type Y, also has a pore size in this range. Types X, Y, and L are distinct, commercially available compositions, well known to those skilled in the art of zeolite chemistry. Type X has a chemical composition expressed in terms of oxide ratios of $Na_2O:Al_2O_3:2-3$ $SiO_2$ with a typical unit cell composition in the hydrated state of $Na_{86}[AlO_2)_{86} (SiO_2)_{106}]\cdot 264\ H_2O$. Type Y, on the other hand, has a composition of $Na_2O:Al_2O_3:>3-6\ SiO_2$. When the $SiO_2:Al_2O_3$ molar ratio is 4.8, the hydrated unit cell composition is $Na_{56}[AlO_2)_{56} (SiO_2)_{136}]\cdot 264\ H_2O$. Both of these zeolites crystallize in the cubic system.

An important building block of these zeolites is the sodalite cage, a truncated octahedron unit consisting of 24 $(Si,AlO_4)$ units. In Type X and Type Y the sodalite cages are connected through 4 of the 8 hexagonal faces in a tetrahedral arrangement. The pores thus created are defined by a 12-member ring of oxygen atoms, approximately 7–9 A in size, opening into a central cavity of about 11 A in diameter.

The preferred synthetic zeolites are types X and Y because of their larger pore sizes. The ability of the Y type to withstand higher temperatures without losing its crystalline structure makes it the most preferred zeolite catalyst for this invention.

The zeolites, as prepared, generally contain as the cation about 13 percent by weight sodium (as $Na_2O$) or equivalent amount of other alkali metal. As explained above, this cation may be replaced with other cations to reduce the sodium content. In this invention the zeolite catalyst contains less than 10 percent alkali metal (expressed as $Na_2O$), preferably less than 5 percent and more preferably less than 3.0 percent by weight.

The most preferred catalysts are the Type Y synthetic zeolites in which the sodium cation has been exchanged with ammonium, and the catalyst has then been calcined at about 500° C. to remove ammonia, producing essentially a protonated Type Y sieve, in which the sodium content (expressed as $Na_2O$) has been reduced below about 3% by weight. Examples of commercially available zeolites of this type are the Linde LZ-Y62, LZ-Y72, and LZ-Y82 molecular sieve catalysts marketed by Union Carbide Corporation.

An example of the process in which this catalyst is used to advantage is described below. Impure dimethyl sulfide (by-product from the manufacture of methyl mercaptan) and $H_2S$ are fed continuously in a molar ratio ranging from about 1 to 10 to about 1 to 20. The reactants are vaporized in preheaters, mixed, and passed into a reactor containing zeolite catalyst. Elevated temperatures, in the range 250°–400° C., and pressures from atmospheric to 600 psig are used to effect reaction. The crude product from the reactor is passed into a series of at least two continuous distillation towers (or columns), where the excess unreacted $H_2S$ is separated in one tower and recycled to the reactor; high-purity methyl mercaptan is separated as an overhead product in another tower; and (optionally) any unconverted impure dimethyl sulfide collected as a tower-bottoms product can be recycled to the reactor for further conversion to methyl mercaptan. It is the particular advantage of the zeolite catalyst of this invention that it is active at relatively low temperatures, and at short contact times, for converting dimethyl sulfide and $H_2S$ to methyl mercaptan, thus obviating the need for a reaction-promoter such as carbon disulfide. Lower reaction temperatures and high throughput rates may be used, with a concomitant saving of energy, and the distillation and recycling operations of the continuous process are greatly simplified by the elimination of the need for a reaction-promoter.

Operable conditions for the desired reaction to occur in the reactor are the presence of a zeolite catalyst of Type X, Type Y, or Type L, containing less than 10% of an alkali metal (expressed as $Na_2O$), a catalyst-bed temperature in the range 250°–450° C., and pressures ranging from atmospheric to 600 psig. A molar excess of $H_2S$ over dialkyl sulfide is required for high conversions to alkyl mercaptan, but the molar ratio of $H_2S$ to dialkyl sulfide may range from about 3/1 to 20/1. The rate at which the dialkyl sulfide is passed over the zeolite catalyst may range from about 10 to about 300 gram-moles of dialkyl sulfide per kilogram of catalyst per 24 hours.

The preferred catalyst-bed temperatures are in the range 320°–390° C. and the preferred pressures in the reactor are in the range 50–350 psig. The preferred molar ratio of $H_2S$ to dialkyl sulfide is in the range 5/1 to 15/1. The preferred rate at which the dialkyl sulfide is passed over the zeolite catalyst is in the range 50–150 gram-moles of dialkyl sulfide per kilogram of catalyst per 24 hours, or (in a commercial operation) 50–150 pound-mols of dialkyl sulfide per one-thousand pounds of catalyst per 24-hour day. The most preferred dialkyl sulfide for which this process is to be used is dimethyl sulfide, with the reaction product being methyl mercaptan.

The following example is intended to illustrate the process of this invention and to demonstrate the advantage of the zeolite catalysts but not intended to limit the invention thereto.

EXAMPLE 1

In this example the use of a preferred synthetic zeolite catalyst, Union Carbide's LZ-Y62 (Example 2), is compared with the use of a prior-art (U.S. Pat. No. 2,667,515) catalyst, cadmium sulfide on alumina (Example 1), for converting dimethyl sulfide and $H_2S$ to methyl mercaptan.

Liquid dimethyl sulfide was pumped at a measured rate and $H_2S$ was metered as a gas through a flowmeter. The reactants were mixed just above and passed downward through the vertically mounted reactor. The reactor was a 316 stainless steel, single tube, fixed-bed type, heated externally with an electric furnace.

The reactor was equipped with a sliding vertical thermocouple probe going up the center of the catalyst bed. Temperatures recorded are the hot spot temperatures in the bed. All runs were carried out at atmospheric pressure. The crude reaction product exiting from the bottom of the reactor was passed as a vapor through heated stainless steel tubing directly into the heated gas-sampling device of a gas chromatograph for analysis. The total weight percent dimethyl sulfide converted (to all products) and the percent molar conversion of dimethyl sulfide to methyl mercaptan were calculated from the gas chromatographic analysis of the single-pass crude product stream.

The catalyst in the reactor is Union Carbide's Linde LZ-Y62 molecular sieve (zeolite), ⅛" extrudate, which is manufactured by ammonium-exchanging a conventional (sodium) Type Y sieve and calcining it to remove ammonia and produce essentially a protonated Type Y sieve.

Dimethyl sulfide (DMS) and H$_2$S were reacted in a 1/10 molar ratio at atmospheric pressure. Catalyst-bed temperatures ranging from 320° C. to 425° C. were examined. A DMS mole velocity equivalent to 60 gram-moles of DMS per kilogram of catalyst per 24 hours was used for all runs with the zeolite catalyst. The results are given in Table 1 below.

TABLE 1

| | ZEOLITE CATALYST (INVENTION) | | |
|---|---|---|---|
| Run No. | Catalyst Bed Temperature, °C. | Total DMS Converted (weight %) | % Molar Conversion (DMS → 2CH$_3$SH) |
| 1 | 320 | 56 | 56 |
| 2 | 345 | 58 | 58 |
| 3 | 375 | 70 | 65 |
| 4 | 400 | 74 | 62 |
| 5 | 425 | 75 | 59 |

Appreciable quantities of methane were identified in the crude product stream at the higher catalyst bed temperatures in the range 400°–425° C.

In a similar manner and with similar results as in the above Example 1, diethyl sulfide is converted with H$_2$S to ethyl mercaptan; di-tertiary-butyl sulfide, to tertiary butyl mercaptan; di-cyclohexyl sulfide, to cyclohexyl mercaptan; di-n-octyl sulfide, to n-octyl mercaptan; and di-n-dodecyl sulfide, to n-do-decyl mercaptan.

For comparative purposes, cadmium sulfide on alumina catalyst was prepared according to the procedure described in Example 1 of U.S. Pat. No. 2,677,515, charged into the reactor, and evaluated over the preferred range of conditions disclosed in that patent. Accordingly, dimethyl sulfide and H$_2$S were reacted at atmospheric pressure, with a molar ratio of H$_2$S to dimethyl sulfide of 10/1, catalyst-bed temperatures ranging from 345° C. to 440° C., and a dimethyl sulfide (DMS) pumping rate (mole velocity) equivalent to 10 gram-moles of DMS per kilogram of catalyst per 24 hours. The results are shown in TABLE 2 below.

TABLE 2

| | CADMIUM CATALYST (U.S. Pat. No. 2,667,515) | | |
|---|---|---|---|
| Run No. | Catalyst Bed Temperature, °C. | Total DMS Conversion (Weight %) | % Molar Conversion (DMS → 2CH$_3$SH) |
| 1 | 345 | 50 | 50 |
| 2 | 395 | 54 | 54 |
| 3 | 415 | 56 | 54 |
| 4 | 435 | 59 | 53 |
| 5 | 440 | 60 | 48 |

At catalyst-bed temperatures in range 415°–440° C., methane was identified as a by-product in the crude product stream.

A comparison of the data in TABLES 1 and 2 shows that substantially higher conversions of dimethyl sulfide to methyl mercaptan are obtained with the zeolite catalyst, compared to the prior art cadmium sulfide on alumina catalyst, at temperatures below 400° C., and at a mole velocity (pumping rate) that is six times greater than that used with the CdS/Al$_2$O$_3$ catalyst. The unconverted DMS from one pass over the zeolite catalyst can be recycled to the reactor to achieve ultimate methyl mercaptan yields (based on DMS) of 94% or higher (at 320°–375° C.).

What is claimed:

1. A continuous vapor-phase process for preparing high purity $C_1$ to $C_{18}$ alkyl mercaptan, RSH, comprising reacting dialkyl sulfide, R—S—R, where R is $C_1$ to $C_{18}$ alkyl or $C_6$ to $C_{18}$ cycloalkyl, with a molar excess of hydrogen sulfide in the presence of a zeolite catalyst at elevated temperatures not in excess of 390° C., said zeolite catalyst being Type X, Type Y, or Type L, and containing less than 10% by weight alkali metal, expresed as Na$_2$O.

2. The process of claim 1, wherein R is $C_1$ to $C_{12}$ alkyl.

3. The process of claim 1 wherein R—S—R is crude, by-product from a methyl mercaptan manufacturing process.

4. The process of claim 1, wherein the catalyst temperature is in the range 250°–390° C.

5. The process of claim 4, wherein the pressure in the reaction zone ranges from atmospheric to 600 psig.

6. The process of claim 4, wherein the molar ratio of hydrogen sulfide to dialkyl sulfide supplied to the reaction zone ranges from 3:1 to 20:1.

7. The process of claim 4, wherein the rate at which the dialkyl sulfide is passed over the catalyst ranges from 10 to 300 gram-moles of dialkyl sulfide per kilogram of catalyst per 24 hours.

8. The process of claim 4, wherein the alkali metal content of the zeolite catalyst has been reduced below 10% by exchanging the alkali metal ions with protons or catalytically active cations.

9. The process of claim 4, wherein the alkali metal has been reduced below 10% by exchanging the alkali metal ions with ammonium ions and thereafter the zeolite is calcined to remove at least a major portion of the ammonia.

10. The process of claim 9, wherein the alkali metal content, expressed as Na$_2$O, is below 3% by weight.

11. The process of claim 10, wherein the dialkyl sulfide is dimethyl sulfide and the reaction product is methyl mercaptan.

12. The process of claim 11, wherein the catalyst temperature is in the range 320°–390° C. and the pressure in the reaction zone is in the range 50–350 psig.

13. The process of claim 12, wherein the dimethyl sulfide is passed over the zeolite catalyst at a rate in the range of 20–150 gram-moles per kilogram of catalyst per 24 hours, and the molar ratio of hydrogen sulfide to dimethyl sulfide supplied to the reactor is in the range 5:1 to 15:1.

* * * * *